(12) United States Patent
Blakeley, III

(10) Patent No.: US 7,168,316 B2
(45) Date of Patent: Jan. 30, 2007

(54) HUMIDITY METER WITH NON-CONTACT TEMPERATURE MEASUREMENT

(75) Inventor: Gerald W. Blakeley, III, Lincoln, MA (US)

(73) Assignee: Extech Instruments Corporation, Waltham, MA (US)

( * ) Notice: Subject to any disclaimer, the term of this patent is extended or adjusted under 35 U.S.C. 154(b) by 0 days.

(21) Appl. No.: 11/039,653

(22) Filed: Jan. 19, 2005

(65) Prior Publication Data

US 2005/0178199 A1    Aug. 18, 2005

Related U.S. Application Data

(60) Provisional application No. 60/537,557, filed on Jan. 20, 2004.

(51) Int. Cl.
| | |
|---|---|
| G01N 29/02 | (2006.01) |
| G01N 19/10 | (2006.01) |
| G01J 5/00 | (2006.01) |
| G01K 1/08 | (2006.01) |

(52) U.S. Cl. .............. 73/335.02; 73/29.01; 73/335.01; 73/29.04; 73/29.05; 374/121; 374/124; 374/142; 374/208

(58) Field of Classification Search .............. 73/29.01, 73/335.01, 335.02, 29.04, 29.05; 374/120, 374/121, 124, 130, 141, 142, 208
See application file for complete search history.

(56) References Cited

U.S. PATENT DOCUMENTS

| | | | | |
|---|---|---|---|---|
| 5,011,296 | A | * | 4/1991 | Bartosiak et al. ............ 374/131 |
| 5,626,424 | A | * | 5/1997 | Litvin et al. ................. 374/121 |
| 6,095,682 | A | * | 8/2000 | Hollander et al. ........... 374/121 |
| 6,442,953 | B1 | * | 9/2002 | Trigiani et al. ................ 62/130 |

FOREIGN PATENT DOCUMENTS

| | | | |
|---|---|---|---|
| GB | 2288878 A | * | 11/1995 |
| JP | 3-202733 A | * | 9/1991 |

\* cited by examiner

*Primary Examiner*—Daniel S. Larkin
(74) *Attorney, Agent, or Firm*—Brian M. Dingman, Esq.; Mirick, O'Connell, DeMallie & Lougee

(57) ABSTRACT

A humidity meter with non-contact temperature measurement capability, including a humidity meter contained at least partially in a housing and having outputs relating to measured humidity parameters including humidity and ambient temperature, an output display contained in the housing, for displaying measurements to a user, a non-contact optically-based temperature sensing device coupled to the housing, having an output related to sensed temperature, and circuitry contained in the housing for processing both the humidity meter outputs and the temperature sensing device output, and transmitting the processed output to the output display.

20 Claims, 5 Drawing Sheets

HUMIDITY METER WITH NON-CONTACT TEMPERATURE MEASUREMENT

CROSS REFERENCE TO RELATED APPLICATION

This application claims priority of Provisional application Ser. No. 60/537,557, filed on Jan. 20, 2004.

FIELD OF THE INVENTION

This invention relates to a humidity meter that is typically used for measuring relative humidity and related parameters, also having non-contact infrared (IR) temperature measurement capabilities.

BACKGROUND OF THE INVENTION

There are many situations in which technicians and others need to accomplish both non-contact temperature measurement along with measurement of relative humidity and related parameters. Humidity meters are typically used to measure parameters including (but not necessarily limited to) relative humidity (RH) and ambient temperature. The ambient temperature measuring sensor is usually located in the same enclosure as the humidity measuring sensor in order to be able to determine dew point or other parameters. This prevents or reduces the ability to use the temperature measuring device to make a contact temperature measurement. In addition, very often there is a need to measure surface temperatures that cannot be easily accessed with a contact type measuring device. Present practices require the use of two different instruments, typically a humidity meter and a thermometer or pyrometer, to perform both humidity meter and surface temperature measurement tasks.

SUMMARY OF THE INVENTION

It is therefore a primary object of this invention to provide an instrument that can be used to measure both humidity parameters and temperature. Many of the functions of these measurements, such as the display, power supply, housing, and analog to digital converter, can be common to both the humidity meter or hygro-thermometer functionality and the surface temperature measurement functionality. With the invention, portability is improved by only having to carry one instrument for use in the field. To further simplify use for quick field measurements, in a preferred embodiment there is no need to relocate the humidity enclosure for the temperature measurement function.

This invention features a humidity meter or hygro-thermometer with non-contact temperature measurement capability. The humidity meter is contained in a housing, and has outputs relating to measured humidity parameters, including, but not limited to humidity and ambient temperature. There is also an output display contained in the housing, for displaying results to a user. A non-contact, optically-based temperature sensing device is coupled to the housing, and has an output related to non-contact sensed temperature. Circuitry contained in the housing processes both the humidity meter outputs and the non-contact, optically-based temperature sensing device output, and transmits the processed outputs to the output display.

The humidity meter is preferably a digital humidity meter. The non-contact, optically-based temperature sensing device preferably comprises an infrared sensor. The infrared temperature sensing device may further comprise a lens, proximate the infrared sensor, for focusing entering radiation and protecting the infrared sensor from damage. The infrared temperature sensing device may define a sense axis that is fixed relative to the housing, or adjustable relative to the housing. When adjustable, the temperature sensing device may be mounted in a mount that is coupled to and movable relative to the housing (for example rotatable), to allow the user to aim the non-contact temperature sensing device.

The humidity meter with non-contact temperature measurement capability may further comprise an optical aiming device coupled to the housing, to assist the user in aiming the non-contact temperature sensing device at an object whose temperature is to be measured. The optical aiming device may define an aiming axis that is adjustable relative to the housing, which may be accomplished with the optical aiming device mounted in a mount that is coupled to and movable relative to the housing (e.g., rotatable), to allow the user to aim the optical aiming device. The optical aiming device preferably comprises a diode laser device.

The humidity meter may further comprise a user-operable switch for switching at least some of the circuitry between the humidity meter outputs and the infrared temperature sensing device output. The humidity meter may also include a user-operable switch for selectively routing the infrared temperature sensing device output to the circuitry, or for selectively holding the sensed temperature. The humidity meter also includes an ambient temperature measuring device located in near proximity to the humidity sensing device. These two in sum allow measurement of parameters including, but not limited to, ambient temperature, relative humidity, heat index, and dew point. The humidity and ambient temperature sensing devices may be mounted in a separate removable enclosure that may be used to measure parameters remote from the location of the meter housing, or alternately may be enclosed in the meter housing.

BRIEF DESCRIPTION OF THE DRAWINGS

Other objects, features and advantages will occur to those skilled in the art from the following description of the preferred embodiments, and the accompanying drawings, in which.

DESCRIPTION OF THE PREFERRED EMBODIMENTS OF THE INVENTION

In the invention, the common functions required for processing of signals from an infrared (IR) temperature sensor, and those of a digital humidity meter (RHM), are accomplished by common circuitry, and a common display and other parts as described above. The RHM housing can be designed to include the IR sensing element, and an optional laser aiming device.

Figure 1:
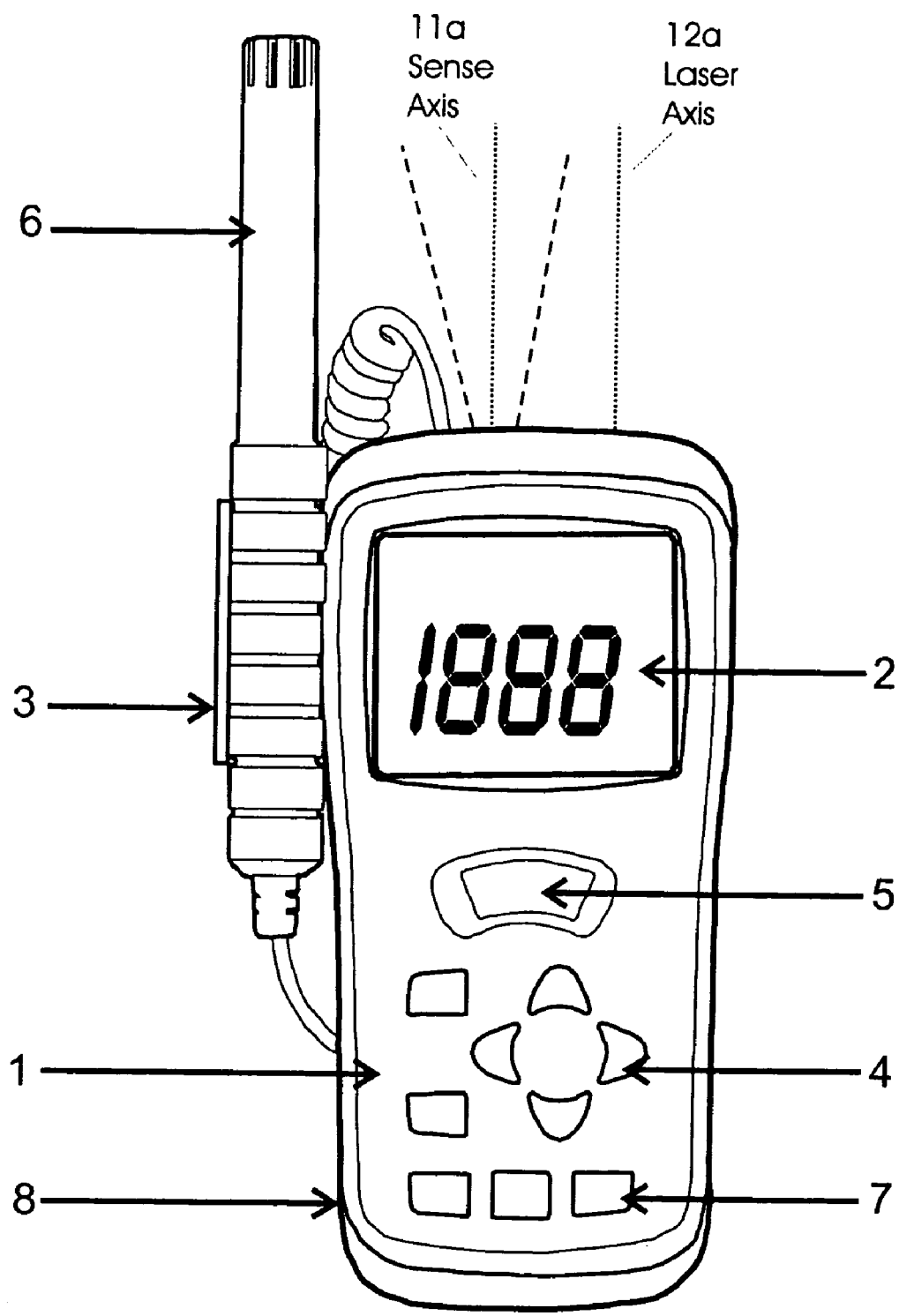
FIG. 1 is a top view of a preferred embodiment of the humidity meter with non-contact temperature measurement according to this invention.
Figure 2:
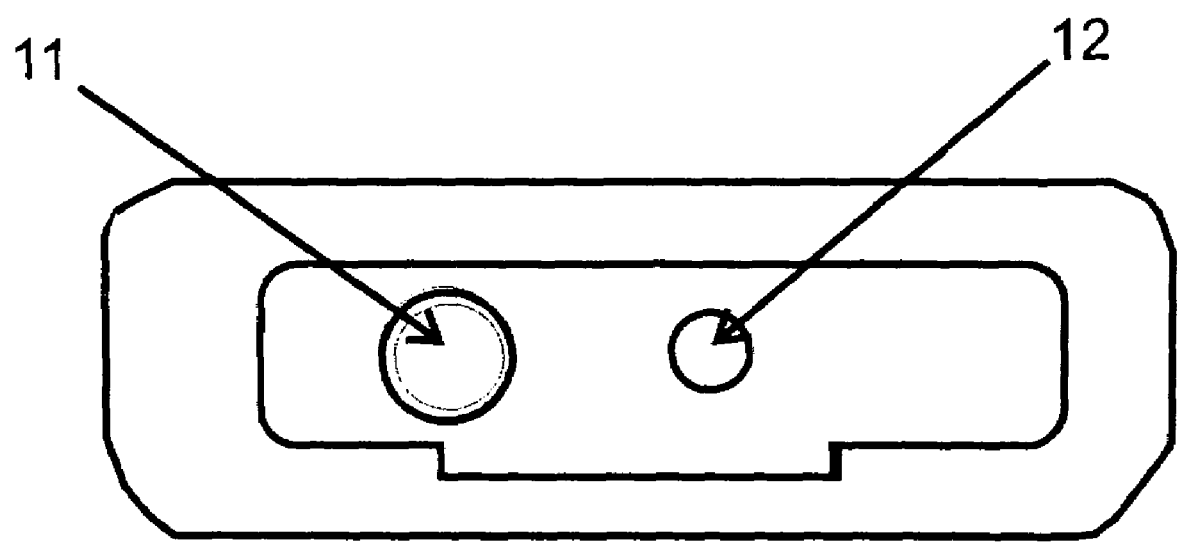
FIG. 2 is an end view of the device of FIG. 1.

A typical mechanical arrangement of the invention is shown in FIGS. 1 & 2. FIG. 1 is a top view of a typical arrangement consisting of a housing or case 1 that contains the circuitry in a convenient hand-held unit, with a digital display 2 for reading the values being measured. Pushbutton switches 4 allow the user to select one of a multiplicity of functions with a multiplicity of ranges. Pushbutton switches 7 perform further selection of parameters or functions, in combination with pushbuttons 4, related to the ambient temperature measurement. Pushbutton switch 5 can be used to turn on the laser aiming device and to accept the reading from the IR detector as opposed to the humidity meter inputs. In other embodiments, this pushbutton may also be used to control the IR temperature readout, such as holding the temperature reading while the switch is engaged. Other types of keypads, switches and locations may be used. Since the IR temperature sensor must be pointed at the surface being measured, the display may not be easily viewable by the user while the temperature is being sensed. Thus, it may be desirable that the IR reading be taken and then held on the display for easy reading later, while the IR temperature sensor is pointed away from the surface.

Other embodiments may use these pushbuttons in combination, or alone, to achieve the same result. In addition (and not shown in the drawings) slide switches, rotary switches and/or keypads may also be used. The humidity sensor and the ambient temperature sensor devices may be mounted in an enclosure 6 which is connected to the humidity meter by a cable, in order that the humidity and ambient temperature measurements may be made remotely from (but near to) the meter. A clip 3 is provided to temporarily secure the sensor enclosure to the humidity meter for storage, or to make a local measurement. The cable may also be eliminated by use of many types of wireless communication devices. In other embodiments, the humidity sensor and the ambient temperature sensor devices may be mounted permanently to the humidity meter enclosure or case, without using a separate enclosure.

FIG. 2 is an end view that shows one arrangement of the infrared (IR) detector 11, used to measure the temperature of a surface or body without actual contact. It accomplishes this by detecting the IR emissions given off by the object whose surface temperature is being measured. At a specific temperature, the IR emissions from any object vary with its surface conditions, such as finish and color. This variation is a factor called emissivity. Each type of surface has an emissivity ranging from zero to one. The emissivity of a matte black body is one. The emissivity of this embodiment of the invention is fixed, preferably at 0.95, although other emissivities could also be used. Most objects typically being measured have an emissivity reasonably close to 0.95. Other embodiments may provide means for adjusting the emissivity to improve the measurement accuracy. FIG. 2 also shows an aperture 12 through which a laser beam or another IR sensor aiming beam may be shone (typically from a laser diode) to assist in aiming the IR temperature measurement apparatus at the surface being measured.

Figure 3:
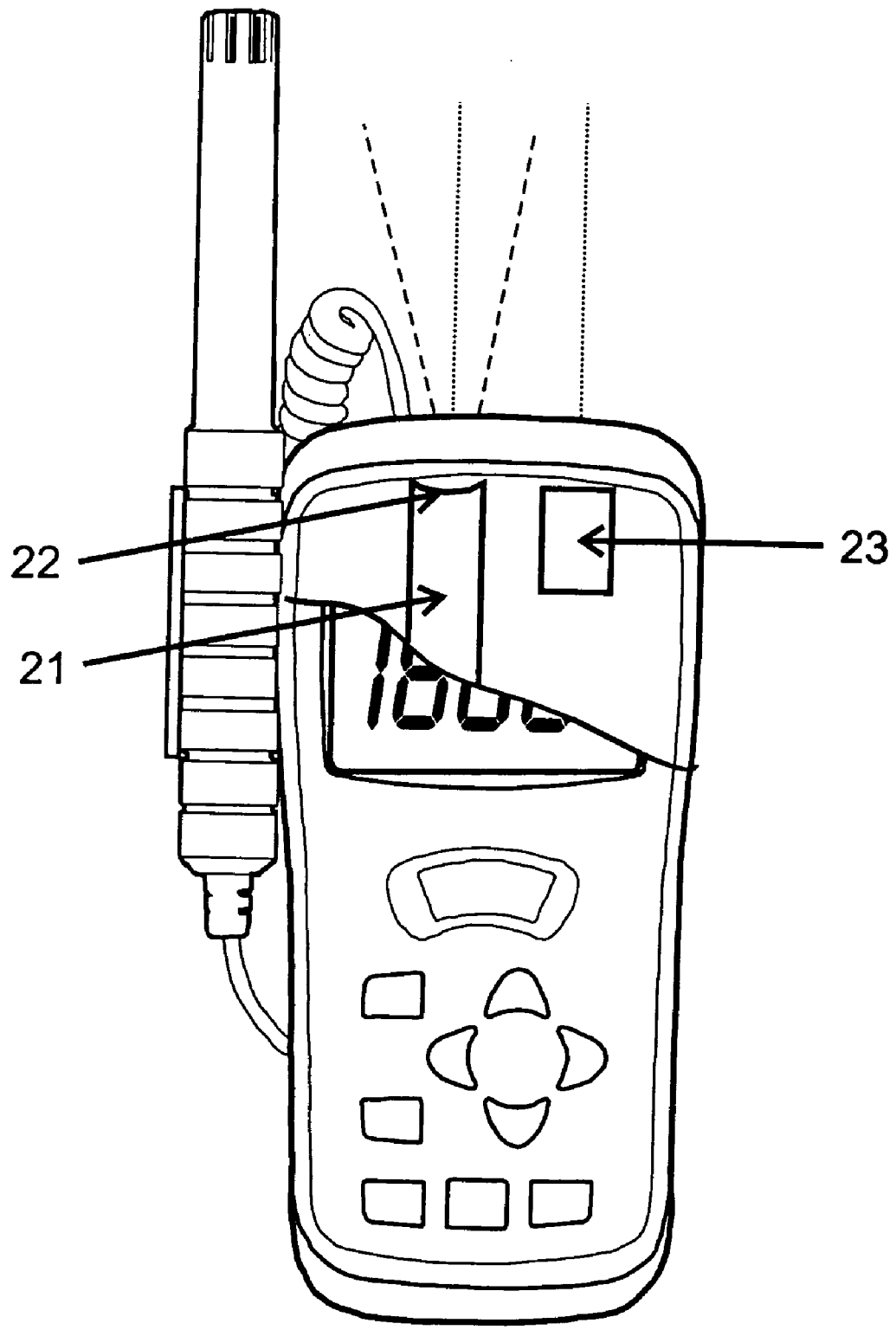
FIG. 3 is a partial cross-sectional view similar to that of FIG. 1.
Figure 4:
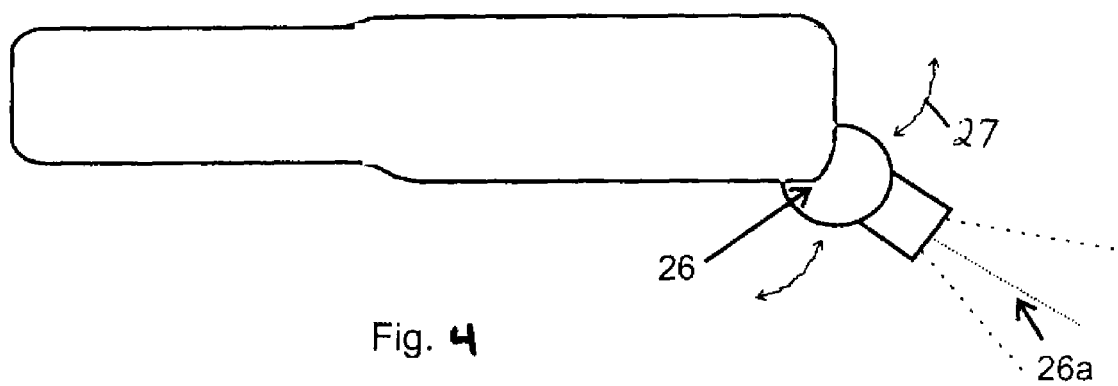
FIG. 4 is a side view of an alternative embodiment to that depicted in FIGS. 1-3, in which the temperature sensing takes place along a different axis.
Figure 5:
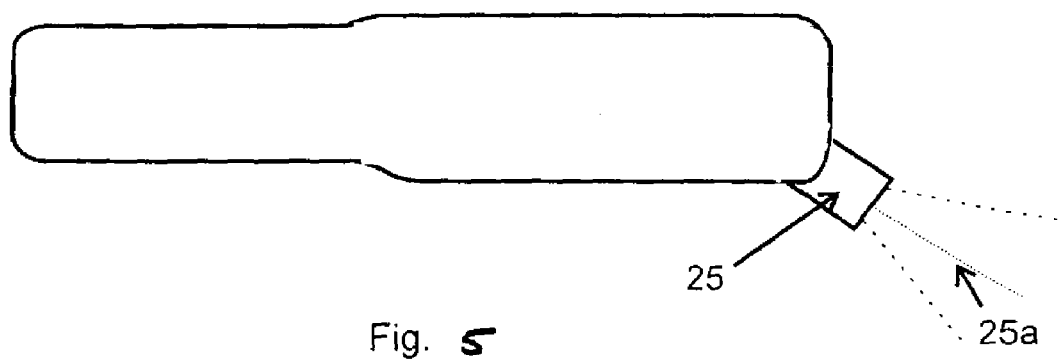
FIG. 5 is a view similar to that of FIG. 4 but for another alternative embodiment with a user-adjustable temperature sensing axis.

IR detector 11, sense axis 11a and laser diode beam sense axis 12a are normally fixed at a slight angle to each other to reduce parallax at the surface being measured. FIG. 3 is a partial cross-sectional view from the top of a typical arrangement of IR detector 21, and aiming laser 23. IR detector 21 may be focused, filtered and protected by lens 22. Other embodiments may have the IR detector and aiming laser mounted at a more convenient angle as shown by combination 25 having sense axis 25a in the side view of FIG. 5. These may also be mounted on a movable (for example rotatable gimbaled) mount 26 with sense axis 26a, as shown in FIG. 4. Mount 26 can move in a uniaxial or multiaxial direction as represented by arrow 27, in order to allow the user to vary the temperature measurement axis.

There may also be included with any of the above a protective covering, holster, or boot 8, as shown in FIG. 1, preferably made of a softer material to protect against mechanical damage and provide a better hand gripping surface.

Figure 6:
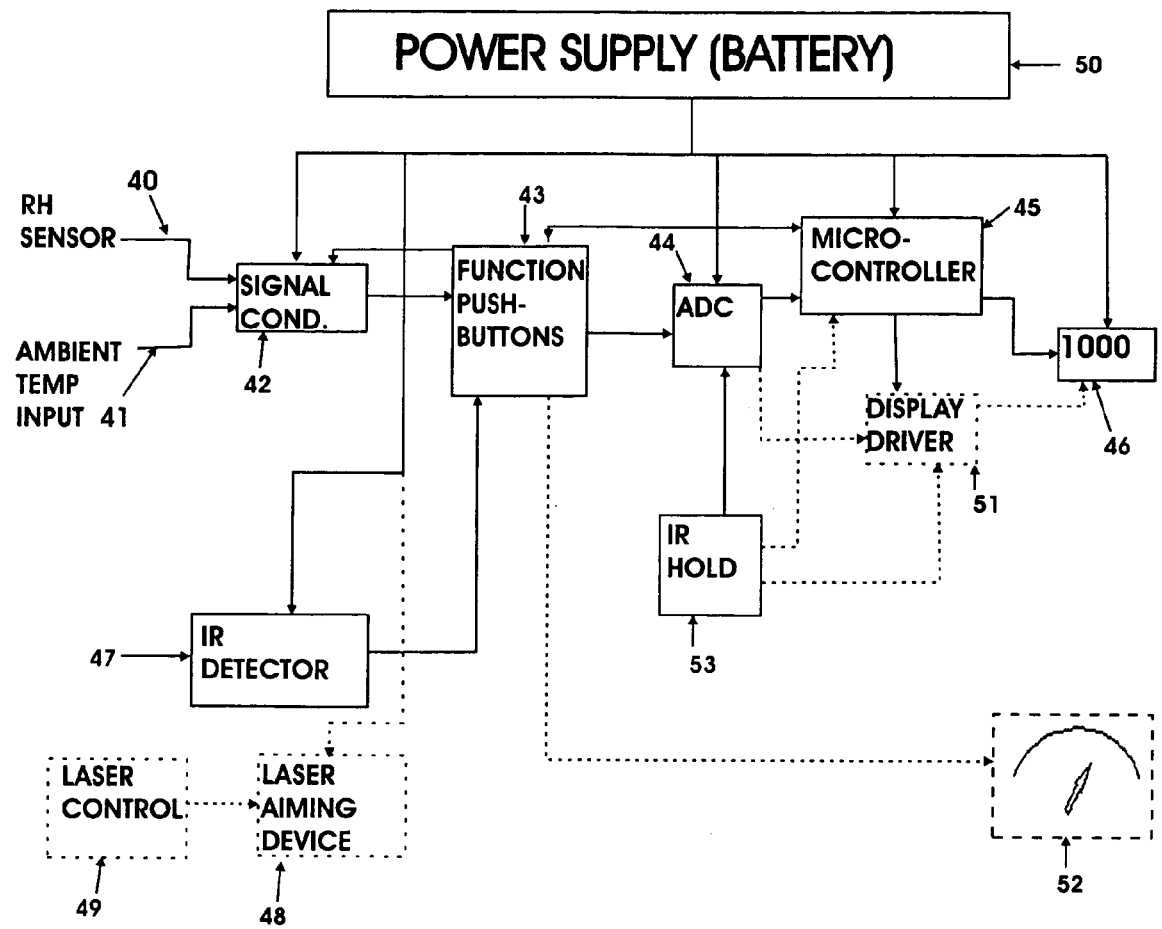
FIG. 6 is a schematic diagram of the circuit functions for the preferred embodiment of this invention.

FIG. 6 is a diagram of the circuit functions of the preferred embodiment, and shows the commonality of the devices shared by both the humidity meter functions and the IR measuring function. Humidity sensor input signal 40 and ambient temperature sensor device input signal 41 are processed by signal conditioning circuits 42, which are selected by pushbuttons 43, under control from microcontroller 45, for presentation to analog to digital converter (ADC) 44. Function pushbuttons 43 may also control the switching of attenuators, gain or other means to convert the measured signal to a more useful one. In alternate embodiments, the signal conditioning function may be located after the function pushbuttons, or divided in front of and between the function pushbuttons and the ADC. The output from the ADC may go directly to display drivers 51, which may also be part of ADC devices, or to microcontroller circuit 45. Microcontroller circuit 45 may also contain the ADC and/or display drivers. Digital displays 46 are driven directly from the microcontroller or the display drivers.

IR detector circuit 47 is also switched to the ADC by the function pushbuttons, similar to the humidity meter input signals. Power supply 50, which usually consists of one or multiple batteries and regulating devices, provides power and reference signals as required to all of the functions described above. Other embodiments may provide a laser aiming device 48 and its control circuit 49, an IR hold circuit 53 which will hold the measured reading on the display, or may also use an analog display 52 which would not require the use of an ADC or other digital circuits.

Although specific features of the invention are shown in some drawings and not others, this is not a limitation of the invention, as the various features can be combined differently to accomplish the invention. Other embodiments will occur to those skilled in the art and are within the following claims.

What is claimed is:

1. A humidity meter with non-contact temperature measurement capability, comprising:
   a humidity meter contained at least partially in a housing and having outputs relating to measured humidity parameters including humidity and ambient temperature;
   an output display contained in the housing, for displaying measurements to a user;
   a non-contact optically-based temperature sensing device comprising an optical aiming device coupled to the housing, to assist the user in aiming the non-contact optically-based temperature sensing device at an object whose temperature is to be measured, the optical aiming device comprising a laser that is adjustable relative to the housing, and the non-contact optically-based temperature sensing device having an output related to sensed temperature; and circuitry contained in the housing for processing both the humidity meter outputs and the temperature sensing device output, and transmitting the processed output to the output display.

2. The humidity meter with non-contact temperature measurement capability of claim 1, in which the humidity meter comprises one or more humidity or temperature sensing devices that are mounted in an enclosure that is separate from the housing and can be located some distance from the humidity meter housing.

3. The humidity meter with non-contact temperature measurement capability of claim 1, in which the humidity meter is a digital humidity meter.

4. The humidity meter with non-contact temperature measurement capability of claim 1, in which the non-contact temperature sensing device comprises an infrared sensor.

5. The humidity meter with non-contact temperature measurement capability of claim 4, in which the non-contact temperature sensing device further comprises a lens, proximate the infrared sensor, for focusing entering radiation onto the infrared sensor.

6. The humidity meter with non-contact temperature measurement capability of claim 1, in which the non-contact temperature sensing device defines a sense axis that is fixed relative to the housing.

7. The humidity meter with non-contact temperature measurement capability of claim 1, in which the non-contact temperature sensing device defines a sense axis that is adjustable relative to the housing.

8. The humidity meter with non-contact temperature measurement capability of claim 7, in which the non-contact temperature sensing device is mounted in a mount that is coupled to and movable relative to the housing, to allow the user to aim the non-contact temperature sensing device.

9. The humidity meter with non-contact temperature measurement capability of claim 8, in which the non-contact temperature sensing device mount is rotatably coupled to the housing.

10. The humidity meter with non-contact temperature measurement capability of claim 1, in which the optical aiming device is mounted in a mount that is coupled to and movable relative to the housing, to allow the user to aim the optical aiming device.

11. The humidity meter with non-contact temperature measurement capability of claim 10, in which the optical aiming device mount is rotatably coupled to the housing.

12. The humidity meter with non-contact temperature measurement capability of claim 1, in which the optical aiming device comprises a diode laser device.

13. The humidity meter with non-contact temperature measurement capability of claim 1, further comprising a switch for switching at least some of the circuitry between the humidity meter outputs and the non-contact temperature sensing device output.

14. The humidity meter with non-contact temperature measurement capability of claim 1, further comprising a user-operable electrical device for selectively routing the temperature sensing device output to the circuitry.

15. The humidity meter with non-contact temperature measurement capability of claim 1, further comprising a user-operable electrical device for selectively holding the sensed non-contact temperature.

16. A digital humidity meter with non-contact temperature measurement capability, comprising:

a digital humidity meter contained at least partially in a housing and having outputs relating to measured humidity parameters including humidity and ambient temperature;

a digital output display contained in the housing, for displaying measurements to a user;

a non-contact infrared temperature sensing device comprising an optical aiming device coupled to the housing, to assist the user in aiming the non-contact infrared temperature sensing device at an object whose temperature is to be measured, the optical aiming device comprising a laser that is adjustable relative to the housing. and the non-contact infrared temperature sensing device having an output related to sensed temperature; and circuitry contained in the housing for processing both the humidity meter outputs and the non-contact temperature sensing device output, and transmitting the processed output to the output display.

17. The humidity meter with non-contact temperature measurement capability of claim 16, in which the humidity meter comprises one or more humidity or temperature sensing devices that are mounted in an enclosure that is separate from the housing and can be located some distance from the humidity meter housing.

18. The humidity meter with non-contact temperature measurement capability of claim 16, in which the non-contact temperature sensing device defines a sense axis that is adjustable relative to the housing.

19. The humidity meter with non-contact temperature measurement capability of claim 18, in which the non-contact temperature sensing device is mounted in a mount that is coupled to and movable relative to the housing, to allow the user to aim the temperature sensing device.

20. The humidity meter with non-contact temperature measurement capability of claim 16, in which the optical aiming device is mounted in a mount that is coupled to and movable relative to the housing, to allow the user to aim the optical aiming device.

* * * * *